United States Patent
Allen et al.

(10) Patent No.: US 6,545,190 B2
(45) Date of Patent: Apr. 8, 2003

(54) ONE STEP PROCESS FOR PREPARING A 1,3-DIOL

(75) Inventors: Kevin Dale Allen, Katy, TX (US); Joseph Broun Powell, Houston, TX (US); Paul Richard Weider, Houston, TX (US); John Frederick Knifton, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/963,068

(22) Filed: Sep. 25, 2001

(65) Prior Publication Data

US 2003/0040647 A1 Feb. 27, 2003

Related U.S. Application Data

(63) Continuation-in-part of application No. 09/808,974, filed on Mar. 15, 2001.

(51) Int. Cl.⁷ .................... C07C 27/00; C07C 29/00
(52) U.S. Cl. .................................................. 568/867
(58) Field of Search ............................ 568/867, 862, 568/866, 861

(56) References Cited

U.S. PATENT DOCUMENTS

| | | | |
|---|---|---|---|
| 3,456,017 A | 7/1969 | Smith et al. ............ | 260/602 |
| 3,463,819 A | 8/1969 | Smith et al. ............ | 260/602 |
| 3,687,981 A | 8/1972 | Lawrence et al. ....... | 260/340.7 |
| 5,256,827 A | 10/1993 | Slaugh et al. ........... | 568/454 |
| 5,304,686 A | 4/1994 | Slaugh et al. ........... | 568/496 |
| 5,304,691 A * | 4/1994 | Arhancet et al. ........ | 568/867 |
| 5,344,993 A | 9/1994 | Slaugh et al. ........... | 568/454 |
| 5,459,299 A | 10/1995 | Cheng .................... | 219/267 |
| 5,463,144 A | 10/1995 | Powell et al. ........... | 568/867 |
| 5,463,145 A | 10/1995 | Powell et al. ........... | 568/867 |
| 5,463,146 A | 10/1995 | Slaugh et al. ........... | 568/862 |
| 5,545,765 A | 8/1996 | Slaugh et al. ........... | 568/862 |
| 5,545,766 A | 8/1996 | Powell et al. ........... | 568/862 |
| 5,545,767 A | 8/1996 | Weider et al. ........... | 568/867 |
| 5,563,302 A | 10/1996 | Weider et al. ........... | 568/862 |
| 5,689,016 A | 11/1997 | Weider et al. ........... | 568/862 |

OTHER PUBLICATIONS

U.S. patent application Ser. No. 09/808,974, Knifton et al., filed Mar. 15, 1998.
U.S. patent application Ser. No. 60/291,826, Knifton et al., filed May 18, 2001.
U.S. patent application Ser. No. 60/291,827, Knifton et al., filed May 18, 2001.

* cited by examiner

*Primary Examiner*—Deborah D. Carr
*Assistant Examiner*—Elvis O. Price

(57) ABSTRACT

Disclosed is a one step hydroformylation process for preparing a 1,3-diol, comprising the reaction of an oxirane with syngas at hydroformylation conditions in an inert solvent in the presence of a hydroformylation catalyst comprising a ruthenium (+1)-phosphine bidentate: cobalt (−1) complex, wherein the ligated metal is ruthenium, under conditions which preferably upon completion of the oxirane/syngas reaction cause a phase separation of the reaction mixture into a solvent phase which is rich in catalyst and a second phase which is rich in the 1,3-diol, recycling the phase rich in catalyst directly to the hydroformylation reaction for further reaction with previously unreacted starting materials, thus permitting valuable hydroformylation catalyst to be recycled without degradation or exposure to downstream processing and recovering the 1,3-diol from the second phase rich in 1,3-diol.

22 Claims, 1 Drawing Sheet

ONE STEP PROCESS FOR PREPARING A 1, 3-DIOL

This application is a continuation-in-part of application Ser. No. 09/808,974, filed Mar. 15, 2001, the entire disclosure of which is hereby incorporated by reference.

FIELD OF THE INVENTION

This invention relates to the synthesis of an reaction rates at high yields via the disclosed use of solvent, phase separation, and recycle of EO, solvent and other components. One or more liquid-liquid phase separations/extractions prior to thermal recovery of product 1,3-PDO optimizes the use of valuable hydroformylation catalysts.

BACKGROUND OF THE INVENTION

Aliphatic 1,3-diols, particularly 1,3-propanediol, have many applications as monomer units for polyester and polyurethane, and as starting materials for the synthesis of cyclic compounds. For example, CORTERRA® polymer is a polyester characterized by outstanding properties that is made of 1,3-propanediol (hereafter 1,3-PDO) and terephthalic acid. There is much interest in the art in finding new routes for synthesizing 1,3-PDO that are efficient, economical, and demonstrate process advantages.

U. S. Pat. Nos. 3,463,819 and 3,456,017 teach the hydroformylation of ethylene oxide to produce 1,3-propanediol and 3-hydroxypropanal (hereafter 3-HPA) using a tertiary phosphine-modified cobalt carbonyl catalyst. U.S. Pat. No. 3,687,981 discloses a process for synthesizing 1,3-PDO. In this process phase separation of intermediate product hydroxyethyl hydroxy dioxane occurs at room temperature, or cooler, before the material goes on to hydrogenation to product. U.S. Pat. Nos. 5,256,827; 5,344,993; 5,459,299; 5,463,144; 5,463,145; 5,463,146; 5,545,765; 5,545,766; 5,545,767; and, 5,563,302, 5,689,016, all assigned to Shell, disclose cobalt catalyzed hydroformylation of ethylene oxide.

U.S. Pat. No. 5,304,691, assigned to Shell, discloses a method of hydroformylating ethylene oxide to 3-hydroxypropanal and 1,3-propanediol in a single step using an improved catalyst system comprising a cobalt-tertiary phosphine ligand in combination with a ruthenium catalyst. In '691 1,3-PDO and 3-HPA are produced by intimately contacting an oxirane, particularly ethylene oxide (EO), a ditertiary phosphine-modified cobalt carbonyl catalyst, a ruthenium catalyst promoter, and syngas (carbon monoxide and hydrogen) in an inert reaction solvent at hydroformylation reaction conditions. A PDO yield of up to 86–87 mole % is reported, using a catalyst comprising cobalt ligated with 1,2-bis (9-phosphabicyclononyl) ethane as bidentate ligand, and either triruthenium (0) dodecacarbonyl or bis[ruthenium tricarbonyl dichloride] as cocatalyst. Also see U.S. Pat. No. 5,304,686, assigned to Shell, which discloses the synthesis of 3-hydroxypropanal using a ditertiary phospine-modified cobalt carbonyl catalyst and a catalyst promoter.

Copending U.S. patent application Ser. Nos. 09/808,974, filed Mar. 15, 2001; Ser. No. 60/291,826, filed May 18, 2001; Ser. No. 60/295,769, filed Jun. 4, 2001; and Ser. No. 60/291,827, filed May 18, 2001, all incorporated herein by reference in the entirety disclose ligated bimetallic catalyst compositions useful in the one step synthesis of 1,3-PDO, and methods for the manufacture thereof.

It would constitute a distinct advance in the art if there were a single-step process for synthesizing 1,3-PDO which could be run as a single phase with sufficient concentration of 1,3-PDO such that upon cooling phase separation could be invoked by temperature reduction, removal of a miscibilizing solvent, and/or addition of a phase split-inducing agent; and the product PDO could be separated from the reaction solvent without the use of high cost extraction or distillation methods, thus permitting valuable hydroformylation catalyst to be recycled without degradation or exposure to downstream processing. Furthermore, it would be extremely efficient, and allow greater flexibility in processing, if residual EO in the crude PDO product could be converted using the product itself as the solvent, and if heavy ends could be purged from the system with minimal impact to the catalyst.

SUMMARY

In accordance with the foregoing, the present invention is a process for synthesizing 1,3-PDO in one step in high yields at commercially viable reaction rates, where recovery of product is preferably accomplished via phase separation of a diol rich phase from the bulk reaction liquor, which comprises the steps of:

(a) Contacting, in a reaction vessel, ethylene oxide, carbon monoxide, hydrogen, a non-water-miscible solvent, and a homogeneous bimetallic hydroformylation catalyst comprising an essentially non-ligated cobalt carbonyl compound and a second Group VIII metal component, preferably selected from the ruthenium or iron, optionally ligated with a ligand selected from a phosphine ligand, a bidentate or multidentate N-heterocyclic ligand, a porphorine ligand; or a phospholanoalkane ligand;

(b) Heating said mixture to a temperature within the range from 30 to about 150° C. and a pressure within the range of about 100 to about 4000 psig for a time effective to produce a single-phase reaction product mixture containing sufficient concentration of 1,3-PDO such that phase separation can be invoked by temperature reduction to result in a phase comprising a major portion of the solvent, at least about 50 wt % of the catalyst composition, plus unreacted ethylene oxide, and a second phase, which comprises a major portion of 1,3-propanediol, a small portion of catalyst, solvent, and heavy ends;

(c) Optionally, instead of or in addition to temperature reduction, inducing phase separation by at least one method selected from removing miscibilizing solvent, or adding a phase split-inducing reagent;

(d) Optionally allowing a two-phase reaction mixture to form during reaction step (b);

(e) Separating said two-phase reaction mixture;

(f) Recycling the phase rich in solvent, catalyst, and unreacted EO, directly to the hydroformylation reaction for further reaction with previously unreacted starting materials;

(g) Directing the second phase to a thermal recovery unit where solvent and catalyst are recycled back to step (a), 1,3-PDO is recovered, and heavy ends are purged.

The present invention is a novel process for synthesizing 1,3-PDO in one-step, which enables operations at commercially viable reaction rates at high yields. At a target 1,3-PDO concentration, the reaction mixture partitions into a predominately solvent phase and a predominately 1,3-PDO phase from which 1,3-PDO can be readily recovered. Crude product PDO separation from the solvent is enabled either during or downstream of reaction via a method selected from temperature reduction, removal of miscibilizing solvent, or addition of a phase split-inducing reagent. PDO product recovery, recycle of residual catalyst, and removal of heavy ends are accomplished primarily through distillation and/or extraction processing.

DETAILED DESCRIPTION OF THE INVENTION

Figure 1:
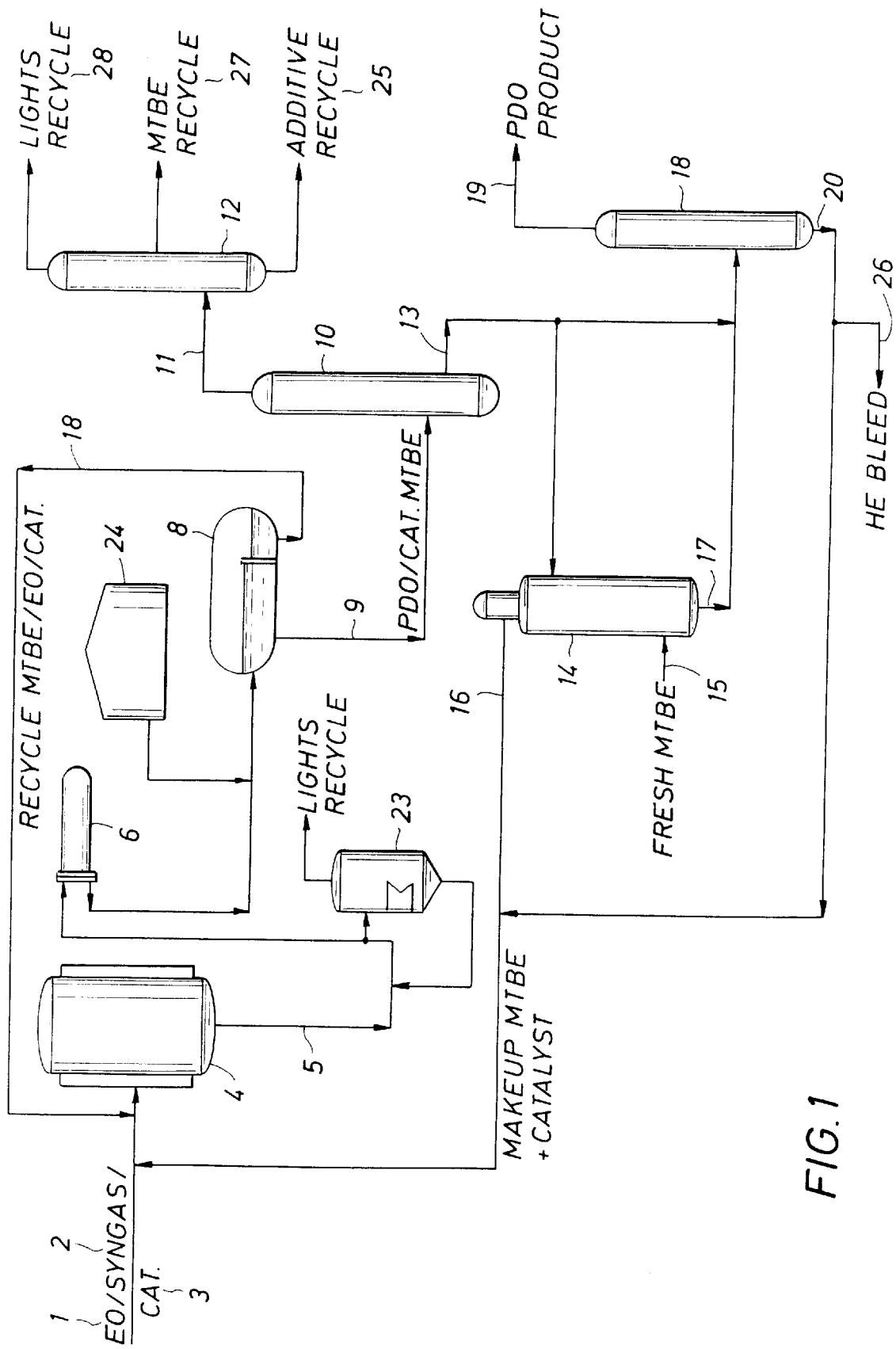
FIG. 1 is a schematic drawing of the process design of the present invention including several optional design features.

In the present invention we have made several surprising discoveries and incorporated them into a new one-step process for synthesizing 1,3-PDO which demonstrates a number of advantages over anything currently available in the art. In the present invention recycling of the reaction solvent and catalyst can be accomplished without prohibitive buildup of miscibilizing side products. In addition residual EO and catalyst that partitions to the separated product can be reacted such that the EO is converted to product.

We have also found that the EO hydroformylation reaction can be run in single phase crude product, as the solvent. Furthermore the reaction can be run to high enough PDO concentrations such that the hydroformylation reaction can occur in a single phase system that upon temperature reduction, or other optional methods of phase induction, can invoke a phase split to a phase comprising solvent, catalyst, and EO, and a second phase comprising a major portion of PDO, under otherwise normal conditions, without destroying the catalyst.

These and other advantages have been incorporated in the present invention by:

1. Using a moderate polarity solvent as the dominant solvent.
2. Improving yields by recycling EO such that the wt % EO is maintained between 0.2 and 20% to maintain rapid rates of reaction and minimize commercial reactor costs, while recovering a majority of the EO leaving the reactor for recycle back to the reaction section.
3. Using one or more liquid phase separations/extractions to facilitate recycle of EO and, most importantly, to enrich one of the liquid phases in PDO relative to catalyst. The process scheme of the present invention allows more efficient separation of PDO via thermal recovery, with less stress on catalyst. In addition, it allows for a significant portion of catalyst to recycle in the PDO-depleted solvent phase, avoiding thermal stress altogether. Furthermore, this allows a purge stream to be taken from the bottoms of the PDO-rich stream after thermal recovery. Degraded catalyst is expected to accumulate in this polar phase, such that one may selectively purge degraded catalyst with heavy reactor byproducts, relative to the total catalyst inventory, thus minimizing usage of very high cost ligated hydroformylation catalyst.
4. Continuing hydroformylation of that fraction of EO that leaves with the PDO-rich phase, vs. with the PDO-lean solvent phase, can provide a means for improving EO yields while not requiring thermal recycle/distillation of EO. Thermal recycle/distillation of EO can present safety hazards. Thus, the liquid-liquid phase separation can be used to recycle a majority of the EO, with continued hydroformylation of that fraction which exits with the PDO-rich phase.
5. Re-extracting the PDO-rich phase under syngas (using makeup moderate polarity solvent) to further improve catalyst and EO recycle.

The invention thus provides a greatly simplified method for conducting a preliminary separation of PDO from recycle catalyst and solvent, thus concentrating the desired PDO product prior to final purification steps. This process utilizes a direct separation of product rather than introduction of possibly a liquid extractant, which would later have to be removed via added distillation capability. This more direct route is thereby less energy intensive and affords a lower capital requirement. Also, catalyst separated from PDO and recycled in this phase split manner is not subjected to stresses associated with recovery via thermal evaporation or distillation, or liquid extractive means.

Using the process of the present invention, catalyst degradation is kept to a minimum, as thermal stress is not applied as in the use of distillation, nor is the entire catalyst inventory subjected to an extraction step. Heavy ends or by-product purging from the system can now be accomplished with minimal impact to the catalyst. Reaction rates can be increased, as higher EO concentrations are possible, with the concept of a "finishing reaction" on the crude PDO product.

The Figure is a schematic diagram of the process. Separate, combined or staged streams of ethylene oxide 1, syngas ($CO/H_2$) 2, and catalyst 3 are charged to a hydroformylation reaction vessel(s) 4, which can be a pressure reaction vessel such as a bubble column or stirred autoclave, operated batchwise or in a continuous mode. The reaction is run to afford a target concentration of 1,3-PDO whereby partitioning of the reaction mixture can be induced by reduction of the temperature to the range of about 0 to 90° C. The reaction mixture from 4, at a temperature of about 80° C. is passed in one embodiment in line 5 to a chiller 6, which is preferably a heat exchanger, is cooled to about 45° C., and is then passed to an unheated settling vessel or separator 8, which can be a weir vessel, mixer-settler, filter bed coalescer or similar vessel. The partitioning and settling can be carried out at a pressure between reaction and ambient, preferably at reaction pressure, and will require residence times within approximately 30 minutes. Following partitioning and settling of the reaction mixture, the phase containing predominantly solvent, unreacted ethylene oxide, and the majority of the catalyst (shown as upper phase) is recycled to the reactor via line 18. The 1,3-PDO-rich phase (shown as lower phase), containing a minor amount of the solvent and minor amounts of byproducts and heavy ends (relative to product), is passed via line 9 to splitter column 10 where light solvents are separated overhead for optional recycle to the reaction. The bottoms 13 from splitter column 10, containing 1,3-PDO and residual catalyst, are directed to column 18 for separation of product 1,3-PDO 19 overheads from higher molecular weight by-products, which exit at 20. Alternatively the bottoms 13 from splitter column 10 can be directed to an optional catalyst extractor 14.

The Figure also shows several optional features in the process design. For higher cost catalyst systems, an option in the current invention is to include a catalyst extractor, 14, that enables recovery of the small amount of catalyst that exits with the product rich phase. In this scheme, fresh or recycled solvent, 27 via 15, flows counter-current with the crude PDO product, 13, in the extractor vessel, 14, promoting intimate liquid-liquid contacting through the use of trays, packing, or forced agitation, such that the solvent extracts active catalyst from the crude PDO product. The recovered catalyst then is routed back to the main reactor 4 via line 16 in a stream of makeup solvent. Also, prior to the separator, 8, in addition to the heat exchanger (cooler), 6, an optional flasher is represented by 23. An optional stream for introducing a phase split-inducing agent is represented by 24. Options for inducing and maintaining a phase split begin with the heat exchanger (cooler), 6, which reduces the temperature of the hydroformylation product stream, such that a phase split will occur under some conditions. The optional flasher 23 can be used to remove miscibilizing cosolvent that has been previously added to induce phase split. The miscibilizing cosolvent may include, for example, short chain alcohols. In stream addition 24 a small amount of phase split-inducing reagent is optionally added to induce the phase split after hydroformylation. The phase split-inducing agent will be a substance that changes the polarity of the mixture, and might include, for example, water, or linear alkanes such as hexane, heptane, or dodecane. Stream 25 is an optional recycle of additives that induce phase split, stream 27 represents separation and recycle of MTBE, and stream 28 represents separation and recycle of additional light solvents.

For any combination of the phase split schemes one obtains a PDO-rich product phase and a recycle solvent rich phase from the phase split unit 8. As mentioned above, the solvent containing most of the unreacted EO and a majority of catalyst is conveniently recycled to the hydroformylation reaction via line 16. Data showing preferential recycle of EO and catalyst is provided in Table 2. The PDO-rich phase (shown as the heavier phase) from 8 is routed to a thermal recovery section, including a splitter column 10, product column 18, and solvent column 12. In the product column 18 PDO is separated overhead 19 and heavy ends plus some residual catalyst leave via 20 with the distillation or evaporator bottoms from 18. Data provided in "% Totals" columns of Tables 2 and 4 show that only a fraction of the catalyst partitions into the PDO-rich phase. This allows heavy ends to be removed via a purge stream 26, while losing significantly less catalyst than would be possible with any other scheme. Thus, loss of expensive one-step catalyst is substantially reduced. Moreover, it is anticipated that the active catalyst will prefer to recycle with the solvent rich phase, while catalyst purged with the bottoms following distillation of the PDO-rich phase will be rich in degraded catalyst, which would preferably be eliminated from the system.

A disadvantage of option 23, entailing a preflash prior to phase split, is that this reduces the amount of EO that can be conveniently recycled, and one must reduce the pressure prior to flash distillation. Other options allow high pressure to be maintained throughout the phase split and recycle steps, which minimizes pumping requirements. Addition of a small amount of phase split-inducing agent after hydroformylation, represented by 24, can help. The phase split inducing agent will exit primarily with the PDO-rich phase, will be recovered in the distillation section, and can therefore be optionally recycled to again initiate a phase split.

As mentioned the addition of a miscibilizing solvent with the subsequent removal is one of the options for controlling the phase split process. Suitable miscibilizing alcohols and agents include, for example, short chain alcohols, such as methanol, ethanol, and isopropanol. For example, one coproduct, ethanol, with an appropriate bulk solvent, can be added as required to bring the product 1,3-PDO up to the desired concentration at reaction temperature.

In the process of the present invention represented by FIG. 1, oxiranes of up to 10 carbon atoms, preferably up to 6 carbon atoms, and ethylene oxide (EO) in particular, may be converted into their corresponding 1,3-diols by the hydroformylation reaction with syngas in the presence of a specified group of hydroformylation catalyst complexes, as will be described below.

The 1,3-diols are made by charging the oxirane, catalyst, optional cocatalyst and/or catalyst promoter and reaction solvent to a pressure reactor with the introduction of syngas (a mixture of hydrogen and carbon monoxide, suitably in a molar ratio of 1:1 to 8:1, preferably 2:1 to 6:1) under hydroformylation conditions.

The process of the present invention may be operated as a batch-type process, continuous process, or mixed forms thereof, however the features of the present invention would permit a continuous one-step process to operate more effectively and efficiently than previously possible. The invention process can be carried out in the continuous mode by maintaining homogeneity in the reaction mixture until a maximum 1,3-PDO concentration is reached. The reaction conditions which permit this mode of operation include an EO concentration in the reaction mixture of at least about 0.5 wt % and avoidance of the formation of byproducts such as light alcohols and acetaldehyde, or use of a flash step to remove said byproducts. Reaction in 2–4 reactors with staged EO addition is preferred for continuous operation.

The reaction process includes conversion of the EO to 1,3-PDO via intermediate 3-hydroxypropanal, which is formed and hydrogenated to 1,3-PDO in-situ. By "in-situ" in this context is meant that conversion of ethylene oxide to 1,3-PDO is carried out without isolation of the intermediate 3-hydroxypropanal and in the presence of a single catalyst system for both hydroformylation and hydrogenation. The reaction is carried out under conditions effective to produce a reaction product mixture containing a target maximum concentration window of 1,3-PDO with relatively minor amounts of 3-hydroxypropanal (HPA), acetaldehyde and heavy ends.

For best results, the process is conducted under conditions of elevated temperature and pressure. Reaction temperatures range from ambient temperature to 150° C., preferably from 50 to 125° C., and most preferably from 60 to 110° C. The reaction pressure (total pressure, or partial pressure if inert gaseous diluents are used) is desirably in the range from 5 to 15 MPa, preferably from 8 to 10 MPa. In a batch process, the reaction will generally be complete within 1.5 to 5 hours.

The reaction solvent is preferably inert, meaning that it is not consumed during the course of the reaction. Ideal solvents for the invention process will solubilize the feed and products during the course of the reaction, but allow phase separation at reduced temperatures. Ideal solvents will exhibit low to moderate polarity such that the 1,3-PDO (produced and converted in-situ) will remain in solution during the course of the reaction but will readily split into distinct phases upon cooling. Suitable solvents are described in U.S. Pat. No. 5,304,691 incorporated herewith by reference in the entirety. Good results may be achieved with ethers, including cyclic and acyclic ethers, optionally in combination with an alcohol or aromatic hydrocarbon.

One group of suitable reaction solvents is alcohols and ethers that can be described by the formula:

Where $R_1$ is hydrogen or $C_{1-20}$ linear, branched, cyclic, or aromatic hydrocarbyl or mono- or polyalkylene oxide and $R_2$ is $C_{1-20}$ linear, branched, cyclic or aromatic hydrocarbyl, alkoxy or mono- or polyalkylene oxide. Preferred reaction solvents can be described by the formula:

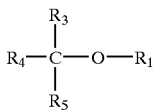

In which $R_1$ is hydrogen or $C_{1-8}$ hydrocarbyl and $R_3$, $R_4$, and $R_5$ are independently selected from $C_{1-8}$ hydrocarbyl, alkoxy, or alkylene oxide. Such ethers include, for example, methyl-t-butyl ether, ethyl-t-butyl ether, diethyl ether, phenylisobutyl ether, ethoxyethyl ether, diphenyl ether, and diisopropyl ether, particularly methyl-t-butyl ether.

The EO will preferably be maintained throughout the reaction in a concentration not less than about 0.2% by weight, generally within the range of 0.2 to 20% by weight, preferably 1 to 10% by weight, based on the total weight of the reaction mixture. The process of the invention can be carried out in a continuous mode, while maintaining said EO concentration, by staged EO addition, for example.

Catalysts useful in the one-step process scheme of the present invention include certain homogeneous bimetallic catalysts comprising an essentially non-litigated cobalt carbonyl compound and a second Group VIII metal component preferably selected from ruthenium or iron compound, optionally ligated with a ligand selected from a phosphine ligand, a bidentate or multidentate N-heterocyclic ligand, a porphorine ligand, or a phospholanoalkane ligand.

Suitable cobalt sources also include salts that are reduced to the zero valence state by heat-treatment in an atmosphere of hydrogen and carbon monoxide. Examples of such salts comprise, for example, cobalt carboxylates such as acetates, octanoates, etc., which are preferred, as well as cobalt salts of mineral acids such as chlorides, fluorides, sulfates, sulfonates, etc. Operable also are mixtures of these cobalt salts. It is preferred, however, that when mixtures are used, at least one component of the mixture be a cobalt alkanoate of 6 to 12 carbon atoms. The reduction may be performed prior to the use of the catalysts, or it may be accomplished simultaneously with the hydroformylation process in the hydroformylation zone.

The preferred catalysts comprise an essentially non-ligated cobalt component and ligated ruthenium compound. These catalyst complexes can be identified by signature absorption peaks on an infrared spectrum of the catalyst composition. The ruthenium may be ligated with a diphosphine ligand, as discussed in copending U.S. patent application Ser. No. 09/808,974, a multidentate or bidentate N-heterocyclic ligand as discussed in copending U.S. patent application Ser. No. 60/291,826, or a class of bis (phospholano)alkane ligands as discussed in U.S. patent application Ser. No. 60/295,769.

The catalysts may be prepared by the stepwise method or the self-assembly method, both of which are discussed briefly below and described in more detail in copending U.S. patent application Ser. No. 09/808,974.

Where the ligand is a N-heterocyclic, a large number of N-heterocyclic compounds have been identified as suitable ligands for the one-step PDO synthesis using the cobalt-ruthenium catalyst couple. Suitable types of bidentate and multidentate N-heterocyclic ligands include, but are not limited to: diazines such as pyrimidine, pyrazine, pyridazine, as well as benzodiazines such as quinazoline and quinoxaline; bispyrldines such as 2,2'-dipyridyl (DIPY), 2,2'-bipyrimidine (BPYM), 1,10-phenanthroline (PHEN), di-2-pyridyl ketone, 4,4'-dimethyl-2,2'-dipyridyl, 5,6-dimethylphenanthroline, 4,7-dimethylphenanthroline, 2,2'-biquinoline, neocuproine, and 2,2'-dipyridylamine; multipyridines such as 2,4,6-tripyridyl-s-triazine (TPTZ), 3,6-di-2-pyridyl-1,2,4,5-tetrazine, 2,2':6', 2"-terpyridine, 2,3-bis (pyridyl)pyrazine, and 3-(2-pyridyl)-5,6-diphenyl-1,2,4-triazine; pyridine, 3-hydroxypyridine, and quinoline, particularly the lower cost homologues derived from coal-tar extracts; and certain 2,6-pyridyl-diimines such as 2,6-bis(N-phenyl, methylimino)pyridine and 2,6-bis[N-(2,6-diisopropylphenyl)methylimino]pyridine.

Preferred heterocyclic compounds for use as ligands include 2,2'-dipyridyl (DIPY), 2,2'-bipyrimidine (BPYM), and 2,4,6-tripyridyl-s-triazine (TPTZ). The structures of these three N-heterocyclics are as follows:

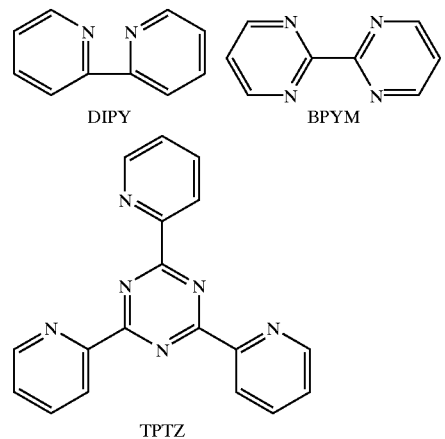

The cobalt counter ion, for best results with N-heterocyclic ligated ruthenium, is believed to be the cobalt tetracarbonyl anion, $([Co(CO)_4]^-)$, having a characteristic cobalt carbonyl IR band in the region 1875 to 1900 $cm^{-1}$, particularly in the region 1888 $cm^{-1}$.

In the case where ruthenium is ligated with a phospholanoalkane, suitable phospholanoalkanes include phospholane substituted alkane compounds of formula I and II as follows:

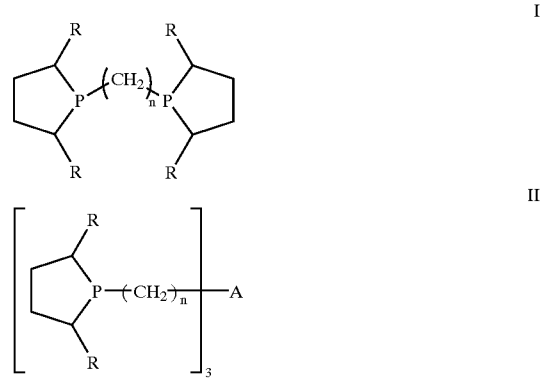

where, in both Formula I and II, R is a lower alkyl, trifluoromethyl, phenyl, substituted phenyl, aralkyl, or ring-substituted aralkyl; and n is an integer from 1 to 12; and for formula II, A is $CCH_3$ CH, N or P. Preferred are compounds of formula I and II wherein R is a lower alkyl of $C_1$ to $C_6$ alkyl and n is 1 to 3. Most preferred are those compounds of formula I and II wherein R is methyl and n is 1 to 3.

Examples of such compounds include, but are not limited to, 1,2-bis(phospholano)ethane, 1,2-bis(2,5-dimethylphospholano)ethane, 1,2-bis[(2R,5R)-2,5-dimethylphospholano]ethane; 1,2-bis[(2S,5S)-2,5- dimethylphospholano]ethane; 1,3-bis(2,5-dimethylphospholano)propane; tris[(2,5-dimethylphospholano)methyl]methane; tris[(2,5-dimethylphospholano)ethyl]amine; or 1,1,1-tris[(2,5-dimethylphospholano)ethyl]ethane. Particularly useful are bidentate, bis(phospholano)alkanes such as, for example, 1,2-bis[(2R,5R)-2,5-dimethylphospholano]ethane (BDMPE), 1,2-bis[(2S,5S)-2,5-dimethylphospholano]ethane, a racemic mixture of the two, plus 1,2 bis(phospholano)ethane.

The cobalt tetracarbonyl anion, [Co(CO)$_4$]$^-$ is also believed to be the counter ion for best results with the phospholanoalkane ligand. However, this ion in the active catalyst can be a modification thereof.

A catalyst system that is very effective and was used in Examples 1 to 14 to demonstrate the phase split process design of the present invention is a ruthenium-modified catalyst characterized by an oxidized ruthenium metal that is ligated by a tertiary diphosphine ligand, as discussed in U.S. patent application Ser. No. 09/808,974 having a, preferably unligated, cobalt compound as counter ion.

The phosphorus ligand is a tertiary diphosphine of the general formula:

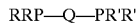

wherein each group R and R' independently or jointly is a hydrocarbon moiety of up to 30 carbon atoms, and Q is an organic bridging group of 2 to 4 atoms in length. The group R or R', when monovalent, may be alkyl, cycloalkyl, bicycloalkyl or aryl, and preferably of up to 20 carbon atoms, more preferably of up to 12 carbon atoms. Alkyl and/or cycloalkyl groups are preferred. The group Q is preferably composed of carbon atoms, which may form part of a ring system such as a benzene ring or a cyclohexane ring. More preferably Q is an alkylene group of 2, 3 or 4 carbon atoms in length, most preferably of 2 carbon atoms in length. A non-limiting list of illustrative diphosphines of this class include 1,2-bis(dimethylphosphino)ethane; 1,2-bis(diethylphosphino)ethane; 1,2-bis(diisobutylphosphino)ethane; 1,2-bis(dicyclohexylphosphino)ethane; 1,2-bis(2,4,4-trimethylpentylphosphino)ethane; 1,2-bis(diethylphosphino)propane; 1,3-bis(diethylphosphino)propane; 1-(diethylphosphino)-3-(dibutylphosphino)propane, 1,2-bis(diphenylphosphino)ethane; 1,2-bis(dicyclohexylphosphino)ethane; 1,2-bis(2-pyridyl, phenylphosphanyl)benzene; 1,2-bis(dicyclopentyphosphino)ethane; 1,3-bis(2,4,4-trimethylpentyphosphino)propane; 1,2-bis(diphenylphosphino) benzene, and the like. These groups R and R' may be substituted with non-hydrocarbon groups themselves. Both groups R and/or both groups R' may also form a ring with the phosphorus atom(s), such as a phosphacycloalkane of from 5 to 8 atoms. Examples on 5-ring systems (phospholano-based ligands) include 1,2-bis(phospholano)ethane, 1,2-bis(2,5-dimethylphospholano) benzene, optically pure (R,R), (R,S), (S,S) 1,2-bis(2,5-dimethylphospholano)ethane or its racemic mixture, and the like. The ring itself may be part of a multiring system. Examples of such ring systems may be found in the aforementioned '691 patent and in WO-A-9842717, incorporated by reference herein in the entirety. In the former phosphabicyclononyl groups are described, in the latter adamantyl-like groups and phosphatrioxatricyclodecyl groups in particular are described. Diphosphines wherein both groups R and R' form a ring with the phosphorus atom are preferred. The most preferred ligands are 1,2-P,P'-bis(9-phosphabicyclo[3.3.1] and/or [4.2.1]nonyl)ethane (hereinafter B9PBN-2), its 1,2-P,P'-propane and/or its 1,3-P,P'-propane analogue (hereinafter B9PBN-3).

Ditertiary phosphine ligands are commercially available. Catalysts prepared therefrom are known in the art and their method of preparation is described in detail in U.S. Pat. Nos. 3,401,204 and 3,527,818, which are both incorporated by reference herein in the entirety. The phosphine ligands may also be partially oxidized to phosphine oxides in the manner described in the '691 patent.

The ratio of phosphine ligand to ruthenium atom may vary from 2:1 to 1:2, preferably from 3:2 to 2:3, more preferably from 5:4 to 4:5 and is most preferably about 1:1. It is hypothesized that this results in a tertiary diphospine ruthenium tricarbonyl compound, but it might also be a bis(tertiary diphosphine ruthenium)pentacarbonyl compound. Unligated ruthenium carbonyl is believed to be an inactive species, and the catalyst preparation therefore seeks to ligate each ruthenium atom.

The counter ion, for best results, is believed to be cobalt tetracarbonyl ([Co(CO)$_4$]$^-$), although the ion in the active catalyst may be a modification thereof. Part of the cobalt compound may be modified with (excess) tertiary diphosphine, e.g., up to 75 mole %, say up to 50 mole % or less. However, the counter ion is preferably the non-ligated cobalt tetracarbonyl mentioned before. Cobalt carbonyls can be generated by reaction of a starting cobalt source such as cobalt hydroxide with syngas, as described in J. Falbe, "Carbon Monoxide in Organic Synthesis", Springer-Verlag, NY (1970), or otherwise.

The oxidation state of the ruthenium atom is not entirely certain (in theory, ruthenium may have a valence of 0 to 8), which may even change during the course of the hydroformylation reaction. Accordingly, the molar ratio of ruthenium to cobalt may vary within relatively broad ranges. Sufficient cobalt (0) should be added to completely oxidize all of the complexed ruthenium employed. An excess of cobalt can be added, but is not of particular value. Suitably, the molar ratio varies from 4:1 to 1:4, preferably from 2:1 to 1:3, more preferably from 1:1 to 1:2.

The reaction mixture will preferably include a catalyst promoter to accelerate the reaction rate. Suitable promoters include sources of mono- and multivalent metal cations of weak bases such as alkali, alkaline earth, and rare earth metal salts of carboxylic acids and tertiary amines. The promoter will generally be present in an amount within the range of about 0.01 to about 0.6 moles per mole of cobalt. Suitable metals salts include sodium, potassium, and cesium acetates, propionates and octoates; calcium carbonate and lanthanum acetate. The preferred promoters, by virtue of their availability and demonstrated promotion of ethylene oxide conversion, are dimethyldodecylamine and triethylamine.

The homogeneous bimetallic catalysts described may be prepared by the step-wise method as discussed in U.S. patent application Ser. No. 09/808,974. It is also within the scope of the invention to prepare the catalyst complex by a self-assembly method wherein all catalyst components are brought together at the same time, but the conditions and, in particular, the solvent, are selected such as to favor the formation of a ligated ruthenium species, rather than a ligated cobalt species.

In the stepwise method, the ligated ruthenium component is prepared first, and then the cobalt carbonyl component and any promoter are added to the ruthenium complex solution. The ruthenium-complex is formed by reaction of a ruthenium carbonyl such as triruthenium dodecacarbonyl with a stoichiometric amount of the selected ligand. The reaction is carried out in a solvent in which any catalyst intermediates are soluble. The solution is heated to a temperature within the range of about 90 to about 130° C., preferably about 100 to about 110° C., under a carbon monoxide atmosphere, for a time sufficient for complete reaction of the ligand with the ruthenium, usually about 1 to about 3 hours. The selected cobalt carbonyl and any promoter used are then added to the solution of ligated ruthenium carbonyl and the solution is maintained at the elevated temperature for a time of about 15 to about 60 minutes.

In the self-assembly method, careful selection of the catalyst precursors and the catalyst preparation solvent are important in obtaining the desired final catalyst composition. It is necessary for the ligand to react with the ruthenium carbonyl prior to the generation of any cobalt (0) carbonyl by reduction. Self-assembly catalyst preparation is carried out by combining, in a solvent, a cobalt salt such as cobalt octanoate, a ruthenium (0) carbonyl such as triruthenium dodecacarbonyl, and a ligand for the ruthenium. The starting ingredients are present in a Co: Ru ratio within the range of about 1:0.15 to about 1:2, preferably 1:2, and a Ru: ligand ratio within the range of about 1:0.16 to about 1:1. The solution is heated at a temperature within the range of about 110 to about 130° C. under a reducing atmosphere such as 1:4 $CO:H_2$ for a time effective for essentially complete ligation of the ruthenium, generally about 1 to about 3 hours.

Whether generated by self-assembly or stepwise, the bimetallic catalysts exhibit specific signature infrared bands, as discussed in copending U.S. patent application Ser. No. 09/808,974. The presence of the Ru-ligated species rather than the (Co-phosphine species may be confirmed by e.g. IR analysis.

In this regard it is emphasized that in the aforementioned U.S. Pat. No. 5,304,691 it was noted that the form of the ruthenium is not critical. Although it is suggested to use ruthenium complexes of phosphines described in this reference, any such use is clearly to prepare tertiary phosphine-complexed cobalt carbonyl catalysts with consequently the loss of the phosphine-complexed ruthenium starting material.

The optimum ratio of oxirane feed to bimetallic catalyst complex will in part depend upon the particular complex employed. However, molar ratios of oxirane to the cobalt within the catalyst complex from 2:1 to 10,000:1 are generally satisfactory, with molar ratios of from 50:1 to 500:1 being preferred.

At the conclusion of the hydroformylation reaction in the present invention, the product mixture is preferably recovered by phase separation followed by several distillation steps to permit recycling of unreacted starting materials, as well as the catalyst and reaction solvent, for further use. The present invention provides a commercially viable process with efficient catalyst recovery and with multiple cycles of essentially complete recycle of catalyst to the reaction. The preferred catalyst recovery process involves separation of the two liquid phase mixture noted previously and recycle of the bulk solvent phase to the reactor and return therewith of at least 60 to 90% by weight of the starting catalyst.

In a preferred manner of running the process, reaction conditions such as oxirane concentration, catalyst concentration, solvent, product concentration, reaction temperature, and the like, are selected such as to achieve a homogeneous reaction mixture at elevated temperatures and cause a partitioning of the reaction mixture into a solvent phase containing much of the catalyst and a second phase containing most of the 1,3-propanediol, upon cooling the mixture. Such a partitioning facilitates isolation and recovery of product, recycle of catalyst, and removal of heavy ends from the solvent system. This process is referred to as a phase separation catalyst recycle/product recovery method.

In the process, the reactor contents are allowed to settle or are transferred to a suitable vessel at or near reaction pressure where, upon slight or considerable cooling, distinct phases may form that are substantially different, being considerably rich in product or in catalyst and solvent. The phase rich in catalyst and solvent is directly recycled for further reaction with feed materials. Product is recovered from the product rich phase by conventional methods.

It is essential that the reaction is run such that product diol maintains concentration levels in the reaction mix suitable for phase separation. For example, concentration of 1,3-propanediol can be between less than 1 and greater than 50% by weight, generally between 8 and 32% by weight and preferably between 16 and 25% by weight.

Temperature during quiescent settling of phases can be between just above the freezing point of the reaction mixture up to at least 150° C. and very likely higher, generally between 27 and 97° C., and preferably between 37 and 47° C.

The EO concentration is maintained to avoid the formation of light alcohols and aldehydes that are miscibilizing agents. Oxiranes will preferably be maintained throughout the reaction in a concentration not less than about 0.2% by weight, generally within the range of 0.2 to 20% by weight, preferably 1 to 10% by weight, based on the total weight of the reaction.

The reaction can be run with a two-phase system. However, yields and selectivities are maximized when high concentrations of product are present in a single phase reaction and subsequent phase separation occurs upon cooling.

In addition to temperature reduction, partitioning of the reaction mixture can be promoted by addition of a phase split-inducing agent. Such an agent will be added to the reaction mixture in an amount within the range of about 2 to 10% wt, preferably 4 to 8% wt based on the total reaction mixture. Suitable agents include, but are not limited to, glycols, such as ethylene glycol, and linear alkanes, such as hexane and dodecane. Partitioning can be accomplished by the addition of 1,3-PDO into the reaction mixture to bring product concentration up to the target proportion. Also, miscibilizing alcohols and agents with similar polarity such as ethanol, propanol and isopropanol can be added initially, then removed prior to, and subsequently induce the phase separation. For example, under normal reaction conditions in methyl-t-butyl ether solvent a homogeneous 1,3-PDO concentration of about 16 wt % at about 70° C. will result in partitioning of the reaction mixture into a solvent-rich phase and a 1,3-PDO-rich phase upon reduction of temperature to about 43° C.

The optimum amount of each phase-inducing agent will vary and can be determined by routine experimentation. For example, hexane induces reaction mixture partitioning when present in methyl-t-butyl ether solvent in a concentration of about 16 wt %, based on total solvent. Ethanol promotes partitioning of the reaction product mixture at a concentration within the range of about 5 to about 8 wt %. Therefore, the primary solvent and any phase-inducing agent will influence the partitioning behavior of the reaction mixture.

Commercial operation will require efficient catalyst recovery with multiple cycles of essentially complete recycle of catalyst to the reaction. The preferred catalyst recovery process involves separation of the two liquid phase mixture noted previously and recycle of the bulk solvent phase to the reactor and return therewith of at least 60 to 90% by weight of the starting catalyst.

The following examples will serve to further illustrate the invention disclosed herein. The examples are intended only as a means of illustration and should not be construed as limiting the scope of the invention in any way. Those skilled in the art will recognize many variations that may be made without departing from the spirit of the disclosed invention.

EXPERIMENTAL

Table 1 lists categories of materials, formulations, and abbreviations used in the examples.

TABLE 1

Materials and formulations

| | | |
|---|---|---|
| Co source | CoOc | Cobalt octoate |
| | DCO | Dicobalt octacarbonyl |
| Ru source | TRC | Triruthenium dodecacarbonyl |
| | BRCC | Bis(ruthenium tricarbonylchloride) |
| Ligand | B9PBN-2 | 1,2-P,P'-bis(9-phosphabicyclononyl)ethane |
| | BDEPE | 1,2-bis(diethylphosphino)ethane |
| | BDIPE | 1,2-bis(diiosbutylphosphino)ethane |
| | BDOPE | 1,2-bis(2,4,4-trimethylpentylphosphino)ethane |
| | BDMPE | (R,R) 1,2-bis(dimethylphospholano)ethane |
| Solvent | MTBE | Methyl-t-butyl ether |
| | T/CB | 5:1 v/v mixture of toluene/chlorobenzene |
| Oxirane | EO | Ethylene oxide |
| Promoter | DMDA | Dimethyldodecylamine |
| | NaAc | Sodium acetate |

EXAMPLE 1

Phase Separation Catalyst Recycle/Product Recovery process with catalyst formed by self-assembly.

In an inert atmosphere drybox, to a 300 ml autoclave, 1.85 grams (5.35 mmole Co) cobalt (II) ethylhexanoate, 1.392 grams (4.48 mmole) 1,2-bis(9-phosphacyclononyl)ethane, 0.509 grams (2.3 mmole Ru) triruthenium dodecylcarbonyl, 145.85 grams methyl-tert-butyl ether (MTBE) and 0.30 grams dimethyldodecyl amine was added. The autoclave body was sealed and fitted to a benchscale process unit. Under a headspace of 4:1 $H_2$:CO ratio syngas at 1500 psig the mixture was allowed to reach equilibrium and preform catalyst over 2 hours at 130° C. Reactor temperature was reduced to 90° C. An addition of 16.96 grams of ethylene oxide (EO) was made and allowed to react with syngas feed at a 2:1 $H_2$: CO ratio until the EO is substantially, but not completely consumed. The reactor content was transferred under reaction conditions to a phase separation vessel where phase separation began immediately. From the vessel, 12.94 grams lower layer material was isolated. The upper layer reaction liquor was recycled back to the reactor. Compositions of the upper and lower layer are given in Table 2. Catalyst partition data is shown in Table 3. The product, 1,3-propanediol, was produced at an average rate of 20 g/L/hr.

EXAMPLE 2

Phase Separation Process, Recycle 1

The recycled reaction liquor from Example 1 was heated to 90° C. An addition of 14.74 grams ethylene oxide was made and allowed to react under a head space of 2:1 $H_2$: CO ratio syngas at 1500 psig until the EO was substantially consumed. The reactor contents were transferred under syngas pressure to a phase separation vessel where phase separation began immediately resulting in the isolation of 8.22 grams of lower layer material. Upper layer reaction liquor was recycled back to the reactor. Compositions of the upper and lower layer are given in Table 2. Catalyst partition data is shown in Table 3. The averaged reaction rate through this recycle gave 14 g/L/hr.

EXAMPLE 3

Phase Separation Process, Recycle 2

The recycled reaction liquor from Example 2 was heated to 90° C. An addition of 14.74 grams ethylene oxide was made and allowed to react under a headspace of 2:1 $H_2$ : CO ratio syngas at 1500 psig. The reactor contents were transferred under syngas pressure to a phase separation vessel where phase separation began immediately and 8.50 grams of lower layer material was isolated. Upper layer reaction liquor was recycled back to the reactor. Compositions of the upper and lower layer are given in Table 3. Catalyst partition data is shown in Table 3. The averaged reaction rate through this recycle gave 37 g/L/hr.

EXAMPLE 4

Phase Separation Process, Recycle 3

The recycled reaction liquor from Example 3 was heated to 90° C. An addition of 14.74 grams ethylene oxide was made and allowed to react under a head space of 2:1 $H_2$:CO ratio syngas at 1500 psig. The reactor contents were transferred under syngas pressure to a phase separation vessel where phase separation began immediately and 19.50 grams of lower layer material was isolated. Upper layer reaction liquor was recycled back to the reactor. Compositions of the upper and lower layer are given in Table 2. Catalyst partition data is shown in Table 3. The averaged reaction rate through this recycle gave 49 g/L/hr.

EXAMPLE 5

Phase Separation Process, Recycle 4

The recycled reaction liquor from Example 4 was heated to 90° C. An addition of 14.74 grams ethylene oxide was made and allowed to react under a head space of 2:1 $H_2$:CO ratio syngas at 1500 psig. The reactor contents were transferred under syngas pressure to a phase separation vessel where separation began immediately and 32.80 grams of lower layer material was isolated. Upper layer reaction liquor was recycled back to the reactor. Compositions of the upper and lower layer are given in Table 2. Catalyst partition data is shown in Table 3. The averaged reaction rate through this recycle gave 34 g/L/hr.

EXAMPLE 6

Phase Separation Process, Recycle 5

The recycled reaction liquor from Example 5 was heated to 90° C. An addition of 14.74 grams ethylene oxide was made and allowed to react under a head space of 2:1 $H_2$:CO ratio syngas at 1500 psig. The reactor contents were transferred under syngas pressure to a phase separation vessel where phase separation began immediately and 71.90 grams of lower layer material was isolated. Upper layer reaction liquor was recycled back to the reactor. Compositions of the upper and lower layer are given in Table 2. Catalyst partition data is shown in Table 3. The averaged reaction rate through this recycle gave 30 g/L/hr.

The three most important results for the phase separation are: 1) achieve an acceptable high enough rate of production of PDO, 2) recycle most of the catalyst (in the upper phase), and 3) recover concentrated product (PDO) in the lower phase.

The data on rate of production of PDO in the examples above shows that an acceptable rate of reaction is achieved and that the catalyst is active after 5 recycles (#1).

Table 3 shows that a high percentage of the catalyst is directly recycled in the upper phase (#2).

Table 2 shows high recovery of PDO in the lower product phase, and high recycle of EO in upper, recycled phase (#3).

TABLE 2

Phase Split Primary Compositions

| Example | Layer | PDO % w | MTBE % w | Mass (g) | % Avail. EO |
|---|---|---|---|---|---|
| 1 | Lower | 59.70 | 18.13 | 12.94 | *— |
| 2 | Lower | 47.97 | 16.60 | 8.22 | *— |
| 3 | Lower | 45.97 | 19.15 | 8.50 | *— |
| 4 | Lower | 47.32 | 21.73 | 19.50 | 7.55 |
| 5 | Lower | 45.16 | 20.99 | 32.80 | 10.55 |
| 6 | Lower | 47.50 | 25.78 | 71.90 | 25.06 |
| 1 | Upper | 4.74 | 85.70 | 152.36 | *— |
| 2 | Upper | 5.15 | 87.16 | 160.04 | *— |
| 3 | Upper | 17.67 | 77.60 | 167.19 | *— |
| 4 | Upper | 27.31 | 54.86 | 163.47 | 92.45 |
| 5 | Upper | 14.41 | 69.85 | 147.04 | 89.45 |
| 6 | Upper | 10.59 | 80.36 | 93.46 | 74.94 |

*Reactions where EO purposefully reacted to extinction

TABLE 3

Catalyst Partitioning Data

| Example | Layer | % of Available Catalyst (Co; Ru) |
|---|---|---|
| 1 | Upper | 90; 88 |
| 2 | Upper | 91; 88 |
| 3 | Upper | 93; 91 |
| 4 | Upper | 82; 75 |
| 5 | Upper | 78; 71 |
| 6 | Upper | 61; 75 |
| 1 | Lower | 10; 12 |
| 2 | Lower | 9; 12 |
| 3 | Lower | 7; 9 |
| 4 | Lower | 18; 25 |
| 5 | Lower | 21; 29 |
| 6 | Lower | 38; 25 |

EXAMPLE 7

PHASE Separation Catalyst Recycle/Product Recovery Process with Catalyst Prepared Via Stepwise Procedure In an inert atmosphere drybox, to a 300 ml autoclave, 2.14 grams (6.90 mmole) 1,2-bis(9-phosphacylononyl)ethane, 0.694 grams (3.25 mmole Ru) triruthenium dodecylcarbonyl, 119 grams methyl tert-butyl ether (MTBE) was added. The autoclave body was sealed and fitted to a benchscale process unit. Under a headspace of 4:1 ($H_2$:CO) syngas at 1500 psig the mixture was allowed to reach equilibrium over 1 hour at 105° C. To the reactor a solution of 1.11 grams (6.50 mmole Co) dicobalt octacarbonyl and 0.108 grams (1.32 mmole) sodium acetate in 33.3 grams MTBE was added at reaction conditions. The catalyst was allowed to preform at 105° C. and 1500 psig for 1.75 hours. Reactor temperature was reduced to 90° C. Two separate additions totaling 13.2 grams of ethylene oxide (EO) were made and allowed to react with a 2:1 ($H_2$:CO) syngas feed until substantially all of the EO was consumed. The reactor contents were transferred under syngas pressure to a temperature controlled phase separation vessel. The phase separation was allowed to equilibrate at 43° C. A lower phase of 36.8 grams was isolated. Upper phase was recycled back to the reactor. Compositions of the upper and lower phase are given in Table 4. Catalyst partition data is shown in Table 5. The product, 1,3-propanediol was produced at an average rate of 26 g/L/hr.

EXAMPLE 8

Phase Separation Process, Recycle 1

The recycled reaction liquor from Example 7 was heated to 90° C. An addition of 14.74 grams ethylene oxide was made and allowed to react under a head space of 2:1 syngas at 1500 psig. The reactor content was transferred under syngas pressure to a phase separation vessel. When equilibrated to 43° C., 28.5 grams of lower phase material was isolated. Upper phase reaction liquor was recycled back to the reactor. Compositions of the upper and lower phase are given in Table 4. Catalyst partition data is shown in Table 5. The averaged reaction rate through this recycle gave 24 g/L/hr.

EXAMPLE 9

Phase Separation Process, Recycle 2

The recycled reaction liquor from Example 8 was heated to 90° C. An addition of 11.00 grams ethylene oxide was made and allowed to react under a head space of 2:1 syngas at 1500 psig. The reactor content was transferred under syngas pressure to a phase separation vessel. When equilibrated to 43° C., 24.8 grams of lower phase material was isolated. Upper phase reaction liquor was recycled back to the reactor. Compositions of the upper and lower phase are given in Table 4. Catalyst partition data is shown in Table 5. The averaged reaction rate through this recycle gave 35 g/L/hr.

EXAMPLE 10

Phase Separation Process, Recycle 3

The recycled reaction liquor from Example 9 was heated to 90° C. An addition of 11.00 grams ethylene oxide was made and allowed to react under a head space of 2:1 syngas at 1500 psig. The reactor contents were transferred under syngas pressure to a phase separation vessel. When equilibrated to 43° C., 19.1 grams of lower phase material was isolated. Upper phase reaction liquor was recycled back to the reactor. Compositions of the upper and lower phase are given in Table 4. Catalyst partition data is shown in Table 5. The averaged reaction rate through this recycle gave 23 g/L/hr.

EXAMPLE 11

Phase Separation Process, Recycle 4

The recycled reaction liquor from Example 10 was heated to 90° C. An addition of 11.00 grams ethylene oxide was made and allowed to react under a head space of 2:1 syngas at 1500 psig. The reactor content was transferred under syngas pressure to a phase separation vessel. When equilibrated to 43° C., 38.9 grams of lower phase material was isolated. Upper phase reaction liquor was recycled back to the reactor. Compositions of the upper and lower phase are given in Table 4. Catalyst partition data is shown in Table 5. The averaged reaction rate through this recycle gave 18 g/L/hr.

EXAMPLE 12

Phase Separation Process, Recycle 5

The recycled reaction liquor from Example 11 was heated to 90° C. An addition of 11.00 grams ethylene oxide was made and allowed to react under a head space of 2:1 syngas at 1500 psig. The reactor content was transferred under syngas pressure to a phase separation vessel. When equilibrated to 43° C., 38.9 grams of lower phase material was isolated. Upper phase reaction liquor was recycled back to the reactor. Compositions of the upper and lower phase are given in Table 4. Catalyst partition data is shown in Table 6. The averaged reaction rate through this recycle gave 17 g/L/hr.

The data on rate of production of PDO in the examples above shows that an acceptable rate of reaction is achieved and that the catalyst is active after 5 recycles (#1).

Table 5 shows that a high percentage of the catalyst is directly recycled in the upper phase (#2).

Table 4 shows high recovery of PDO in the lower phase (#3).

TABLE 4

Phase Split Primary Compositions

| Example | Layer | PDO % w | MTBE % w | Mass (g) | % Avail. EO |
|---|---|---|---|---|---|
| 7 | Lower | 63.68 | 16.15 | 24.80 | 7.03 |
| 8 | Lower | 49.68 | 17.39 | 28.50 | 11.52 |
| 9 | Lower | 68.08 | 18.03 | 24.80 | 13.45 |
| 10 | Lower | 53.34 | 24.31 | 19.10 | 15.97 |
| 11 | Lower | 33.32 | 19.39 | 38.90 | 22.36 |
| 12 | Lower | 30.03 | 25.91 | 29.80 | 33.07 |
| 7 | Upper | 7.20 | 44.63 | 165.07 | 92.97 |
| 8 | Upper | 8.89 | 61.35 | 152.73 | 88.48 |
| 9 | Upper | 36.69 | 48.66 | 139.09 | 86.55 |
| 10 | Upper | 16.88 | 54.86 | 131.42 | 84.03 |
| 11 | Upper | 6.14 | 86.65 | 104.92 | 77.64 |
| 12 | Upper | 27.30 | 34.57 | 88.12 | 66.93 |

TABLE 5

Catalyst Species Partition Data

| Example | Layer | % of Available Catalyst (Co; Ru) |
|---|---|---|
| 7 | Upper | 70; 67 |
| 8 | Upper | 82; 68 |
| 9 | Upper | 85; 72 |
| 10 | Upper | 89; 73 |
| 11 | Upper | 67; 63 |
| 12 | Upper | 73; 73 |
| 7 | Lower | 30; 33 |
| 8 | Lower | 18; 32 |
| 9 | Lower | 15; 28 |
| 10 | Lower | 11; 27 |
| 11 | Lower | 33; 37 |
| 12 | Lower | 27; 27 |

EXAMPLE 13

Recycle of Lower Phase Stepwise Assembled Catalyst

Lower layer samples from Examples 7 and 8, rich in 1,3-propanediol product, were distilled at 90–110° C. under vacuum conditions of 60–4 mm Hg. Collections of methyl tert-butyl ether solvent and 1,3-propanediol were made on the column overhead. Overhead material was greater than 92% 1–3, propanediol. The distillation was carried out such that 75% of the initial charge mass was distilled. A 10 gram sample of the distillation bottoms containing recycled catalyst, some 1–3, propanediol and minor amounts of heavy ends was inventoried into a 300 ml autoclave in an inert atmosphere drybox. To the autoclave was added 74 grams of fresh methyl tert-butyl ether solvent. The autoclave was sealed and fitted to a benchscale process unit. The catalyst liquor was heated to 90° C. with stirring. Under a headspace of 4:1 ($H_2$:CO) syngas, 11.00 grams of ethylene oxide was added and allowed to react. The reactor contents were transferred under syngas pressure to a phase separation vessel where at 45° C. phase separation began. When equilibrated, 12.6 grams of lower phase material was isolated. This lower phase contained 56.47% 1,3-propanediol product. Upper phase reaction liquor was recycled back to the reactor and heated to 90° C. under a syngas feed headspace of 2:1 ($H_2$:CO). To this recycled solvent phase, 11.00 grams of ethylene oxide was added and allowed to react. The reactor contents were transferred under syngas pressure to a phase separation vessel where at 43° C. phase separation began. When equilibrated, 24.5 grams of lower phase material was isolated. This lower phase contained 45.14% 1,3-propanediol product. These reactions afforded an 81% product yield. This proves that the catalyst is robust and still active even after being distilled from the product phase and recycled twice through the upper phase of subsequent reactions.

EXAMPLE 14

Use of Hexane as Phase Split Inducing Agent

In an inert atmosphere drybox, to a 300 ml autoclave, 1.159 grams (3.73 mmole) 1,2-bis(9-phosphacyclononyl) ethane, 0.696 grams (3.27 mmole Ru) triruthenium dodecylcarbonyl, 119 grams methyl tert-butyl ether (MTBE) was added. The autoclave body was sealed and fitted to a benchscale process unit. Under a headspace of 4:1 ($H_2$:CO) syngas at 1500 psig the mixture was allowed to reach equilibrium over 1.5 hour at 105° C. To the reactor a solution of, 1.13 grams (6.50 mmole Co) dicobalt octacarbonyl and 0.108 grams (1.32 mmole) sodium acetate in 33.3 grams MTBE was added at reaction conditions. The catalyst was allowed to preform at 105° C. and 1500 psig for 1.75 hours. Reactor temperature was reduced to 90° C. One addition of 22 grams of ethylene oxide (EO) was made and allowed to react with a 2:1 ($H_2$:CO) syngas feed. The reactor contents were transferred under syngas pressure to a temperature controlled phase separation vessel. The phase separation was allowed to equilibrate at 43° C. A lower phase of 9.746 grams was isolated. Upper phase was recycled back to the reactor. As in a fashion similar to above examples additional ethylene oxide was added to the recycled upper layer and allowed to react followed by a temperature induced phase split. On the third recycle in this example 11.00 grams of ethylene oxide was added and allowed to react at 90° C. and 1500 psig. Transfer to phase separation vessel and subsequent to cooling to 35° C., no phase separation was apparent. Two separate additions of 11.00 gram aliquots of ethylene oxide followed by reaction at stated conditions, and cooling to 33° C. did not produce a 1,3-propanediol concentration where a phase separation could be made. We believe that this reaction produced some by-products, such as ethanol and propanol that are miscibilizing in nature that prevented the phase separation. Addition of 10 grams of hexane while in the reactor at stated conditions followed by transfer to the separation vessel and cooling invoked a phase separation at 77° C. This is one way to change the polarity of the system such that a phase split can be induced. It is even possible to add before or during the reaction miscibilizing agents to ensure a single phase reaction. These miscibilizing agents can then be removed; such as by distillation or flashing, to invoke a phase split for product recovery. After equilibrating to 43° C., the lower layer sample of 92.7 grams was isolated and contained 48% 1,3-propanediol product.

We claim:

1. A process for one-step synthesis of 1,3-propanediol which comprises:
   (a) Contacting in a reaction vessel a mixture of ethylene oxide, carbon monoxide, hydrogen, a non-water-miscible solvent and a hydroformylation catalyst composition;
   (b) Heating said mixture to a temperature within the range from 30 to about 150° C. and a pressure within the range of about 100 to about 4000 psig for a time effective to produce a single-phase reaction product mixture containing 1,3-propanediol; and
   (c) Inducing phase separation by at least one method selected from the group consisting of:
      (i) temperature reduction combined with addition of a phase split-inducing agent to the mixture in an amount sufficient to induce phase separation,
      (ii) temperature reduction combined with first adding a miscibilizing cosolvent to keep the reaction product mixture in a single phase and then removing the miscibilizing cosolvent,
      (iii) first adding a miscibilizing cosolvent to keep the reaction product mixture in a single phase and then removing the miscibilizing cosolvent, and
      (iv) adding a phase split-inducing agent to the reaction product mixture in an amount sufficient to induce phase separation;
   wherein the phase separation results in a first phase comprising a major portion of the non-water-miscible solvent, at least 50 percent of the catalyst composition, plus unreacted ethylene oxide, and a second phase, which comprises a major portion of 1,3-propanediol.

2. The process of claim 1 further comprising the second phase also contains catalyst, solvent, and heavy ends.

3. The process of claim 1 further comprising physically separating the two-phase mixture following the induction of phase separation.

4. The process of claim 3 further comprising recycling the phase rich in catalyst directly to the hydroformylation reaction for further reaction with previously unreacted starting materials.

5. The process of claim 3 further comprising extracting residual catalyst from the second phase, returning said catalyst to the one-step reaction vessel and passing the remaining lower phase containing 1,3-PDO to a means for recovery.

6. The process of claim 5 wherein the means for recovery of 1,3-PDO is a distillation column where product 1,3-PDO is separated from higher molecular weight by-products.

7. The process of claim 5 further comprising separating light solvents from 1,3-PDO and distilling to isolate individual light solvents and optionally recycling individual light solvent back to the reaction.

8. The process of claim 1 further comprising operating the process in a continuous manner.

9. The process of claim 1 wherein the temperature during phase separation is from just above the freezing point of the reaction mixture to at least 150° C.

10. The process of claim 9 wherein the temperature during phase separation is from 27 to 97° C.

11. The process of claim 10 wherein the temperature during phase separation is from 37 to 47° C.

12. The process of claim 1 wherein the concentration of the 1,3-diol is from 1 to 50% by weight.

13. The process of claim 12 wherein the concentration of the 1,3-diol is from 8 to 32% by weight.

14. The process of claim 13 wherein the concentration of the 1,3-diol is from 16 to 20% by weight.

15. The process of claim 1 wherein the ethylene oxide concentration is greater than 0.2% by weight.

16. The process of claim 15 wherein the ethylene oxide concentration is from 0.2 to 20% by weight.

17. The process of claim 16 wherein the ethylene oxide concentration is from 1 to 10% by weight.

18. The process of claim 1 wherein the temperature during phase separation is from just above the freezing point of the reaction mixture to at least 150° C., the concentration of the 1,3-diol is from 1 to 50% by weight, and the oxirane concentration is greater than 0.2% by weight.

19. The process of claim 18 wherein the temperature during phase separation is from 27 to 97° C., the concentration of the 1,3-diol is from 8 to 32% by weight, and the oxirane concentration is from 0.2 to 20% by weight.

20. The process of claim 19 wherein the temperature during phase separation is from 37 to 47° C., the concentration of the 1,3-diol is from 16 to 20% by weight, and the oxirane concentration is from 1 to 10% by weight.

21. The process of claim 1 wherein the miscibilizing cosolvent is selected from the group consisting of short chain alcohols.

22. The process of claim 1 wherein the phase split-inducing agent is selected from the group consisting of water and linear alkanes.

* * * * *